United States Patent
Lam et al.

(10) Patent No.: US 9,802,912 B2
(45) Date of Patent: Oct. 31, 2017

(54) CYCLIC ORTHO ESTER FUEL ADDITIVE

(71) Applicant: AIRBUS OPERATIONS LIMITED, Bristol (GB)

(72) Inventors: Joseph K-W Lam, Bristol (GB); Norman Ratcliffe, Bristol (GB); Benjamin De Lacy Costello, Bristol (GB); Sonia Repetto, Bristol (GB); James Costello, Bristol (GB); David Parmenter, Bristol (GB)

(73) Assignee: AIRBUS OPERATIONS LIMITED, Bristol (GB)

( * ) Notice: Subject to any disclaimer, the term of this patent is extended or adjusted under 35 U.S.C. 154(b) by 20 days.

(21) Appl. No.: 14/786,647

(22) PCT Filed: Apr. 24, 2014

(86) PCT No.: PCT/GB2014/051269
§ 371 (c)(1),
(2) Date: Oct. 23, 2015

(87) PCT Pub. No.: WO2014/174290
PCT Pub. Date: Oct. 30, 2014

(65) Prior Publication Data
US 2016/0068504 A1 Mar. 10, 2016

(30) Foreign Application Priority Data

Apr. 25, 2013 (GB) .................. 1307438.0
Sep. 20, 2013 (GB) .................. 1316763.0

(51) Int. Cl.
*C07D 317/36* (2006.01)
*C10G 29/22* (2006.01)
(Continued)

(52) U.S. Cl.
CPC ......... *C07D 317/36* (2013.01); *B01D 17/047* (2013.01); *C10G 29/22* (2013.01);
(Continued)

(58) Field of Classification Search
CPC ............... C07D 317/36; C10M 105/18; C10N 2230/08; C10N 2240/08; C10L 1/1855;
(Continued)

(56) References Cited

U.S. PATENT DOCUMENTS 2,878,109 A 3/1956 Wood et al.
4,261,702 A 4/1981 Sweeney et al.
(Continued)

FOREIGN PATENT DOCUMENTS

DE 2813827 A1 10/1979
DE 2817455 A1 10/1979
(Continued)

OTHER PUBLICATIONS

Search Report dated Oct. 24, 2013 in Great Britain Application No. 1307438.0.
(Continued)

*Primary Examiner* — James Goloboy
(74) *Attorney, Agent, or Firm* — Hauptman Ham, LLP

(57) ABSTRACT

The invention relates to liquid hydrocarbons containing cyclic ortho esters as dehydrating dehydrating icing inhibitors and to methods of using the compounds. The liquid hydrocarbons include fuels such aviation fuels, lubricants, hydraulic fluids and hydrocarbon solvents.

25 Claims, 6 Drawing Sheets

1 (1)

2 (6 x 10³)

3 (1.8 x 10⁷)

4 (1.1 x 10⁸)

(51) Int. Cl.
  *C10L 1/185* (2006.01)
  *C10L 10/14* (2006.01)
  *C10M 105/18* (2006.01)
  *C10G 33/04* (2006.01)
  *B01D 17/04* (2006.01)
  *C10G 75/00* (2006.01)

(52) U.S. Cl.
  CPC ............ *C10G 33/04* (2013.01); *C10G 75/00* (2013.01); *C10L 1/1855* (2013.01); *C10L 10/14* (2013.01); *C10M 105/18* (2013.01); *C10L 2290/24* (2013.01); *C10N 2230/08* (2013.01); *C10N 2240/08* (2013.01)

(58) Field of Classification Search
  CPC ........ C10G 29/22; C10G 33/04; C10G 75/00; B01D 17/047
  USPC ....................................................... 508/307
  See application file for complete search history.

(56) References Cited

U.S. PATENT DOCUMENTS

| | | | |
|---|---|---|---|
| 4,339,443 A | 7/1982 | Baillie et al. | |
| 4,390,417 A | 6/1983 | Sweeney | |
| 4,395,267 A | 7/1983 | Sweeney | |
| 4,647,288 A | 3/1987 | Dillon | |
| 4,943,383 A | 7/1990 | Avery et al. | |
| 5,194,535 A * | 3/1993 | Koppes | C07D 319/06 525/250 |
| 5,268,008 A | 12/1993 | Kanne | |
| 5,705,087 A | 1/1998 | Mushrush et al. | |
| 2006/0281930 A1* | 12/2006 | Ruwwe | C07D 317/34 549/266 |
| 2012/0116096 A1 | 5/2012 | Kalb | |

FOREIGN PATENT DOCUMENTS

| | | |
|---|---|---|
| EP | 0009348 A2 | 4/1980 |
| RU | 2365617 C1 | 8/2009 |

OTHER PUBLICATIONS

Search Report dated Mar. 19, 2014 in Great Britain Application No. 1316763.0.
ISR and WO in PCT/GB2014/051269 mailed Jun. 23, 2014.
Krompiec et al, "A new method for the synthesis of mixed orthoesters from 0-allyl acetals", Tetrahedron Letters, vol. 50(11), 2009, pp. 1193-1195.
Meerwein et al., "Ueber Tertiare 1,2,4-6,Carboxoniumsalze", Justus Liebigs Annalen Der Chemie, vol. 632, Jan. 1, 1960, pp. 38-55.
Narain et al., "Reactions of ethyl orthoacetate with glycols", Indian Journal of Chemistry, Section B: Organic Chemistry Including Medicinal Chemistry, vol. I7B(2), 1979, pp. 189-191.
Santry et al., "Alkyl group effects on the rate constants and equilibrium constants for formation of cyclic tetrahedral intermediates", Journal of the American Chemical Society, vol. 110, No. 9, Apr. 1, 1988, pp. 2909-2914.
Hartmann et al., "Reaction of 1, 2-glycol cyclic ortho esters with trimethylsilyl azide", Tetrahedron Letters,(6), 1979, pp. 513-516.
Kesslin et al., "Ortho Esters as Water Scavengers", Ind. Eng. Chem. Prod. Res. Dev., vol. 5, Jan. 1, 1966, pp. 27-29.
Soulier et al., "Synthesis of some 2-alkoxy- and 2-aryloxy-1,3-dioxolanes", Journal of Heterocyclic Chemistry, vol. 13 (5), 1976, pp. 1125-1128.
European Examination Report dated Oct. 25, 2016 EP Application No. 14 719 829.5.

* cited by examiner

CYCLIC ORTHO ESTER FUEL ADDITIVE

BACKGROUND OF THE INVENTION

The invention relates to liquid hydrocarbons such as hydrocarbon fuels, hydraulic fluids, lubricants or solvents, comprising cyclic ortho ester dehydrating icing inhibitors. The hydrocarbon fuels include aviation fuels. Methods of inhibiting ice crystal formation and ice inhibiting compounds are also provided.

Solubility of water in the current context refers to the maximum water concentration which can dissolve in any given amount of hydrocarbons at a specific temperature and air humidity; this is strongly dependent upon the chemical composition of the fuel itself [1, 2].

Dissolved water is often a normal component of liquid hydrocarbons and is vaporised on combustion of hydrocarbon fuels. However, free water can freeze and block fuel or other feed lines. The water can also support microbial growth and contribute to corrosion. There is therefore a need to remove water or reduce the amount of ice crystal formation in liquid hydrocarbons.

There is a need to identify kinetically fast, lipophilic water scavengers that can produce on hydrolysis hydrophilic ice inhibitors.

Aviation turbine fuels are largely straight-run distillates of crude oil and their composition comprises, by volume, between 99%–99.5% hydrocarbons, with the remaining fraction of heterorganic components containing the elements S, O and N. Jet fuel is a mixture of many different hydrocarbons; most of them can be grouped into three broad classes: paraffins (or alkanes), naphthenes (or cycloalkartes) and aromatics (or alkylbenzenes) [1, 3, 4]. The proportions of these three classes varies depending upon the source of the crude oil from which the fuel is derived and the refining process. The aromatic content is limited to 25% v/v [5]. The formation of attractive electrostatic interactions between water and π-aromatic systems would account for the enhanced solubility of water in alkylbenzenes relative to both paraffins and naphthenes [4].

The aviation industry uses both hardware and quality control procedures to protect jet fuel from water contamination [1]. However, even if jet fuel enters the fuel tank without free water, this does not prevent its formation.

Indeed, dissolved water present in fuel will precipitate out of solution in the form of micro droplets as the fuel temperature drops through diurnal cycles or during operation as the aircraft climbs to altitude [6, 7]. Water solubility in the fuel decreases by approximately 2 ppm (volume) per 1° C. For example, a temperature change from 20→−10° C. creates ca. 29 ppm (volume) of dissolved water to be liberated as free water, which in 100 tons of fuel amounts to 3.62 L of free water [1].

A second source of free water in fuel tanks derives from the condensation of atmospheric moisture. As fuel is consumed, air is drawn into the fuel tanks through the vent system; the moisture in the air condenses as it comes in contact with the cold fuel and tank surfaces at the end of a long flight [8]. Free water can starve engines, support microbial growth, contribute towards corrosion and furthermore freeze, risking plugging filters in the aircraft. The industry has developed equipment and procedures to mitigate these problems, but challenges remain [1, 3].

The aviation industry uses a variety of additives to counter the detrimental effects of free water. Biocides are added to prevent microbial growth, corrosion inhibitors are used to protect uncoated steel tanks and pipelines from corrosion and improve the lubricity of fuels, and Fuel System Icing Inhibitors (FSII) are added to inhibit ice formation.

Since ethylene glycol monomethyl ether (EGME) was banned because of its toxicity to humans and the environment, the only FSII currently approved for Jet A, Jet A-1, and military fuels is di-ethylene glycol monomethylether (di-EGME) [1, 5]. FSII are hydrophilic substances, dissolving in any free water that forms, disrupting hydrogen-bonding networks responsible for molecular ordering—thereby lowering the freezing point of the liquid by preventing crystallisation [3]. The concentration of di-EGME must be in the range 0.10-0.15% v/v [1,5]. At these concentrations, Trohalaki et al. found that water (0.007% v/v) in jet fuel freezes below −36° C. [9]. Di-EGME has also proved to be an effective deterrent to microbial growth [1].

The aviation industry has identified several problems related to the interaction of FSII and "wet" fuel, which can actually undermine fuel protection.

In addition to being hydrophilic, di-EGME is also hygroscopic—this additional characteristic leads to an uptake of atmospheric water during blending operations which affects its solubility in fuel.

Di-EGME has a very high water-fuel partitioning ratio: it preferentially dissolves in water. This leads to denser water layers separating under gravity with up to 40-50 wt % of di-EGME. Unless replenished, the jet-fuel is essentially "stripped" of its protection against icing.

The presence of di-EGME in the water contained within the fuel alters interfacial properties, and can impair the performance of filters and monitors. Particularly, the separation efficiency of filter/coalescers can be compromised [8].

In addition, FSII are toxic at the concentrations required for effective de-icing. 'Water bottoms' drained from storage tanks, fuel system sumps and filters inevitably contain higher concentration of di-EGME, creating concerns about the handling and disposal of these wastes [10]. FSII are only mildly irritating, but they are rapidly absorbed by the skin. Vapours can cause irritation to the eyes and the respiratory system. Long term effects include damage to the central nervous system, blood, skin, eyes, and kidneys [11]. Di-EGME is biodegradable in wastewater treatment system; however concentrations found in water bottoms could be high enough to disrupt the microbiological process. In the environment, the high oxygen demand required for decomposition results in less available oxygen for aquatic organisms [12].

Liquid hydrocarbons, such as aviation fuels present a number of problems for the selection of water scavenging compounds to be used as dehydrating icing inhibitors.

Aviation turbine fuel is a mixture of thousands of organic compounds; it is therefore critical that the scavenger of choice reacts exclusively with water, a notoriously weak nucleophile. The inventors have identified the alcohol-addition products of aldehydes and ketones (i.e., acetals, hemiacetals, ketals, hemiketals and ortho ester) as potentially possessing the appropriate levels of selectivity and stability for our purposes.

An important consideration is for the compound to be combustible as both scavenger and by-products must be readily combustible and leave no residue.

Because water is a relatively small molecule (molecular mass MM=18 g/mol), a relatively large number of reacting moles of scavenger—assuming a 1:1 reaction stoichiometry—are required to dehydrate the jet fuel. In the example mentioned above, 3.62 L of free water requires ca. 200 mol of scavenger. It is important therefore to ensure that the MM of a candidate scavenger is as low as possible, or possesses multiple reactive sites (higher reaction stoichiometry).

A selective scavenger which is switchable (i.e. on/off) can be stored without degradation (off), and yet be activated (on) when mixed with fuel. This is best achieved by choosing a process that is catalysed by mild acid, a particular consideration when one recognises that many liquid hydrocarbons such as Jet A-1 and some hydraulic fluids are mildly acidic.

The products of reacting one mole of the scavenger with water would ideally produce one equivalent of FSII for optimum fuel protection. Although in principle, it is possible to design an acyclic scavenger which generates up to three equivalents of FSII upon hydrolysis, this would impact upon atom economy. We require then a functional group which can be incorporated into a cyclic system which—post hydrolysis—affords an acyclic alcohol, thereby conserving atom economy.

A water scavenger ideally must be sufficiently hydrophobic to be soluble in, and therefore protect jet fuel—yet the product of the reaction with water must be sufficiently hydrophilic to preferentially partition into residual water to act as an effective FSII.

The use of acetals and ketals derived from sugar mannose for FSII has been explored by Mushrush and co-workers (U.S. Pat. No. 5,705,087). These compounds prove to be stable (up to 2 years in jet fuel) and effective as icing inhibitors, and importantly were found to be environmentally benign and relatively nontoxic at the necessary concentration [10, 13]. Additionally ketals have been used in fuels (U.S. Pat. No. 2,878,109).

Unlike an icing inhibitor, a water scavenger must undergo a chemical reaction at the very low operating temperatures (T) commonly encountered in an aircraft. Such low temperatures can dramatically reduce the kinetic energy of participating molecules, to the point that a chemical reaction slows down or effectively stops. It is necessary then to ensure that the energy barrier to reaction ($E_a$)—is small. This ensures a fast reaction even at low temperatures, which corresponds to a high velocity constant (k). The relationship between temperature, energy of activation and reaction velocity is expressed in the Arrhenius equation (I) [14].

$$k = Ae^{\frac{-Ea}{RT}} \quad (I)$$

By examining the rate constants for a range of candidate scavengers (i.e., acetals, ketals, and ortho esters) with water, the inventors found clear correlations between structure, and the barrier to reaction, Ea (FIG. 1). Hydration rates for acetals increase a thousand fold with the replacement of a single hydrogen atom at the functional carbon atom with an alkyl group (1→2 FIG. 1). A ten thousand fold rate increase accompanies progression to the related ketal (2→3 FIG. 1), and an extra 10 fold to the related ortho ester (3→4 FIG. 1). This important increase in relative rate is readily explained by a steric decompression factor as the tetrahedral intermediate collapses to the trigonal counterpart during the hydrolysis reaction, or by the fact that the rate increase corresponds with the stability of the corresponding dialkoxy carbenium intermediate (see later—Scheme 2) [15].

The fastest rate within the series of alcohol addition products of carbonyl compounds is achieved with the ortho ester 4 (FIG. 1), which is readily hydrolysed because there are three oxygen atoms with lone-pairs which may increase the basicity of the leaving group —ROH (see later—Scheme 2).

In conclusion, ortho esters appear to be the most promising candidate for a dual purpose additive meeting the criteria outlined above. The next step was to examine the feasibility of using the acid catalysed hydrolysis of a low molecular weight ortho ester to dehydrate jet fuel. FIG. 2 shows the complex nature of Jet fuel.

SUMMARY OF THE INVENTION

The inventors have found that selecting cyclic ortho esters allows water to be scavenged in liquid hydrocarbons using the low levels of acid typically found in the fuels. This means that acid catalysts need not be added to the liquid hydrocarbon, thereby reducing corrosion in, for example, fuel tanks and fuel pipes. The cyclic ortho esters allow the production of water soluble reaction products, such as alcohols and esters Which act as anti-freeze agents to reduce the freezing point of water left in the liquid hydrocarbon. These may also have anti microbial activity. Moreover, the reaction products can be tailored to segregate into the different phases of the fuel. The structure of the cyclic ortho ester also lends itself to being altered to increase the rate of reactivity with water in hydrocarbons, thereby further reducing the amount of acid needing to be present in the liquid hydrocarbon and lending itself to be used in hydrocarbons without sufficient levels of acid present. The ability to scavenge water at the same time as producing reaction products having ice inhibiting properties is particularly advantageous.

The invention provides a liquid hydrocarbon comprising a dehydrating icing inhibitor selected from Formula I and Formula II, salts thereof or mixtures thereof;

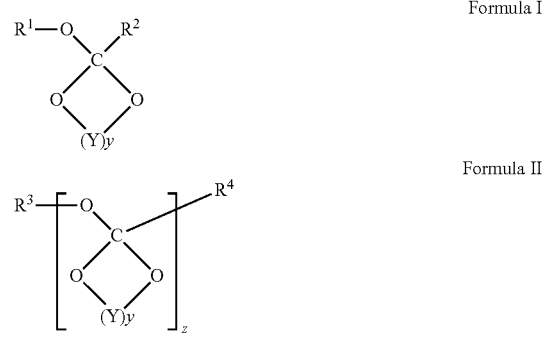

where:
$R^1$ and $R^3$ are independently selectable and are selected from a $C_1$ to $C_6$ substituted or non-substituted, branched or straight chain, alkyl or ether;
$R^2$ and $R^4$ are independently selectable and are selected from a $C_1$ to $C_7$ substituted or non-substituted, straight or branched chain, alkyl;
Y is independently selectable and is a substituted or non-substituted alkyl;
y is an integer of 1 to 3;
z is an integer of at least 2, such as 2 to 6, typically 2

The compounds of the invention are believed to exist in solution as cations such as 1,3,-dioxolan-2-ylium cations. This is shown in FIG. 8 and also discussed in Santry et al J. Am. Chem. Soc. (1998) 110, 2909-2914.

Accordingly such cations may be provided by using salts of the compounds, such as 1,3,-dioxolan-2-ylium salts. The invention therefore also includes within its scope such salts.

The liquid hydrocarbon may be a hydrocarbon fuel, hydrocarbon lubricant, hydraulic fluid or a hydrocarbon solvent. The presence of water in hydraulic fluids or lubricants, such as oils or drilling lubricants, can be a major problem in cold climates where ice can block feed pipes, reduce the efficiency of the lubricant or hydraulic fluid or cause corrosion. Lubricants and hydraulic fluids may be made from, for example, mineral oils or plant or animal fats or oils.

Hydrocarbon solvents (i.e. hydrocarbons used as solvents) include cyclic compounds such as benzene, xylene, cyclohexane, cycloheptane, cyclooctane and cyclopentane; long chain alkanes such as heptane, decane, hexane, octadecane and tridecane; and more complex mixtures of molecules such as turpentine. Often it is desirable to be able to dry the hydrocarbon solvent to remove water. The cyclic ortho esters of the invention may be used for such a purpose.

Hydrocarbon fuels include aviation fuels such as kerosene based Jet A-1 or AVTUR (Ministry of Defense Standard 91-91), Jet A or military jet fuels, gasoline or petrol, diesel and heating oils. Whilst the problem of ice crystal formation in jet fuels is particularly problematic due to aircraft travelling in the cold upper atmosphere, ice crystal formation may also be a problem in colder climates in other fuels.

The liquid hydrocarbon may be mineral or crude oil based. They may also be derived from animal or plant sources including vegetable oils or animal fats. Mixtures of crude oil and biologically derived oils may also be used.

The cyclic ortho ester dehydrating icing inhibitor may be within the hydrocarbon phase, water phase or both phases of the mixture of hydrocarbon and water as the water may be dissolved within the liquid hydrocarbon or separated as a different phase to the hydrocarbon.

$R_1$ and $R_3$ may be selected from $CH_3$—, $CH_3CH_2$—, $CH_3O(CH_2)_a$—, where a is an integer of 1 to 5, and a polyalkylene glycol containing 1 to 6 carbon atoms.

The selection of $R_1$ allows the alcohol reaction product to be changed. If $R_1$ is ethyl, $CH_3CH$—, then ethanol is produced. This is advantageous because ethanol is a component of many fuels, so will burn efficiently. It is also a biocide and has anti-freeze properties. Moreover, the toxicity of ethanol is well characterised. Methanol (from a methyl residue) may be less preferred because of potential toxicity or volatility. However, in some circumstances it may have benefits for it biocidal or solvent properties.

Typically a is 1, 2, 3 or 4.

Alkylene or polyalkylene glycols, such as methylene glycol, ethylene glycol polymethylene or polyethyleneglcols may be used as $R^1$ or $R^3$. Again, the toxicity of polyethyleneglycols (PEG) has been well characterised. Mono-, di- or tri(ethylene glycol) may be used.

$R^2$ and $R^4$ may be independently selected from —$CH_3$, —$CH_2CH_3$, $CH_2CH_2CH_3$, —$CH_2CH(CH_3)_2$ and —$CH_2C(CH_3)_3$.

Changing $R^2$ and $R^4$ can affect the solubility of the reaction product in water or the hydrocarbon. Typically $R^2$ and $R^4$ are $C_1$, $C_2$ or $C_3$ alkyl. However, it has also been noted that using —$CH_2CH(CH_3)_2$ and especially —$CH_2C(CH_3)_3$ has been found to increase the reactivity of cyclic ortho esters with water. This is discussed in the paper by Santry et al (J. Am. Chem. Soc. (1988) 110, 2909-2914) which looked at the effect of alkyl side groups on the reactivity of cyclic compounds. Neopentyl (—$CH_2C(CH_3)_3$) was especially effective. It may also be possible to replace one or more of the remaining hydrogen atoms with additional methyl groups to further modify the reactivity of the cyclic ortho ester.

$R^3$ and $R^4$ may be independently selected and may be methyl or ethyl.

Y is a linker between the two oxygen atoms. It may be independently selectable and may, for example, be —CH— or —CH($CH_3$)—. y may be an integer of 1 to 3. Hence the two oxygen atoms may be linked, for example, by —$CH_2$—, —$CH_2CH_2$— or —$CH_2CH_2CH_2$—, y is typically 2.

z may be an integer of 2 to 6, typically 2 or 3.

The dehydrating icing inhibitor may have formulae III or IV

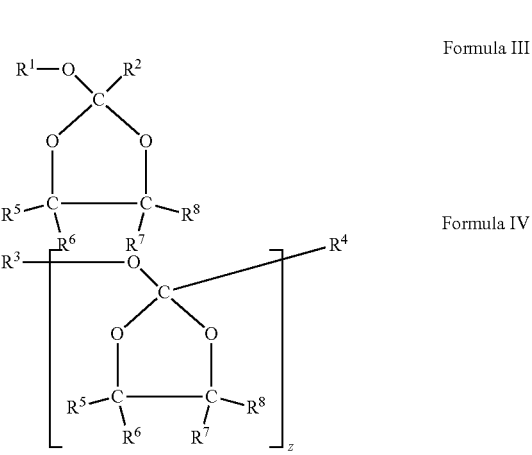

Formula III

Formula IV wherein $R^5$ and $R^7$ are hydrogen; and $R^6$ and $R^8$ are methyl, and wherein $R^6$ and $R^8$ may be cis or trans relative to each other. Alternatively $R^5$ to $R^8$ may all be methyl.

Placing methyl groups on $R^6$ and $R^8$ is expected to increase the reactivity of the cyclic ortho ester with water, thereby reducing the need for an acid catalyst in the liquid hydrocarbon.

Where the liquid hydrocarbon is a jet fuel $R^1$ may be $CH_3CH_2$—, $R^2$ may be a $C_1$-$C_3$ alkyl, y may be —$CH_2$— and y may be 2.

Where insufficient acid is normally found in the liquid hydrocarbon, acid, such a methane sulphonic acid or another acid, may be added to the liquid hydrocarbon.

The term liquid hydrocarbon is intended to mean that the hydrocarbon is liquid at above −50° C., −40° C., −30° C., −20° C. or above −10° C. up to 50° C., 100° C., 120° C., 160° C., 180° C., 200° C., 250° C. or 300° C. depending on the nature of the liquid hydrocarbon. Jet fuel, for example, typically freezes around −36° C. but boils at approximately 160° C. Benzene boils at approximately 80° C. under normal atmospheric pressure.

Typically the liquid hydrocarbon contains 0.01 to 3%, 0.1 to 2% or 0.5 to 1% by volume of the dehydrating icing inhibitor(s).

The dehydrating icing inhibitor typically may have Formula I or III.

Methods of inhibiting ice crystal formation in liquid hydrocarbon using cyclic ortho esters of Formulae I to IV, as defined above, are also provided by the invention.

The liquid hydrocarbon, $R^1$ to $R^8$, Y, y and z may be as defined above.

Compounds of Formulae III and IV are also provided.

BRIEF DESCRIPTION OF THE DRAWINGS

The invention will now be described by way of example only with reference to the following Figures.

DETAILED DESCRIPTION OF SEVERAL EMBODIMENTS

Figure 1:
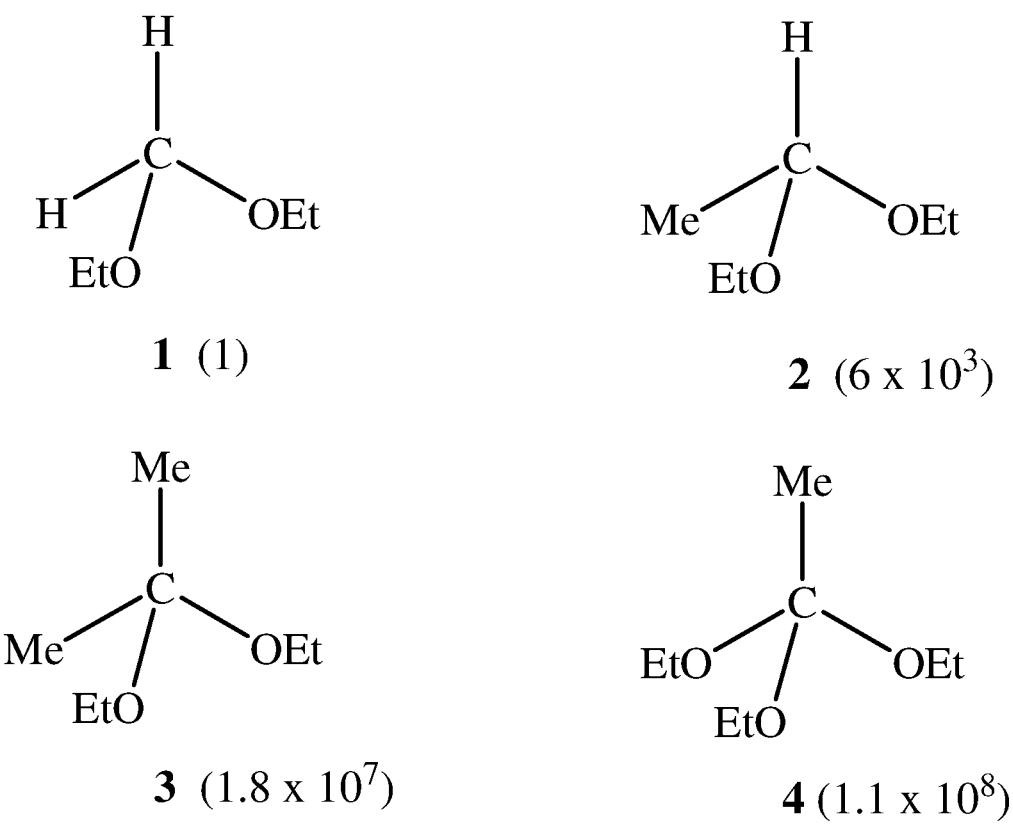
FIG. 1 shows a comparison of the relative rate constants (in parentheses) for the hydration of acetals 1-2, ketal 3 and ortho ester 4.

Acetals, ketals, ortho esters and cyclic ortho esters have been generally known in the art, such as the paper by Santry 1998 Supra, and may be obtained from a number of commercially available source such as Sigma Aldrich.

EXPERIMENTAL SECTION

Experimental GC

The analyses were performed using an Agilent 5890 gas chromatograph equipped with a flame ionisation detector. The GC column used was of fused silica, HP-5MS, 30 m by 0.25 mm, with a helium flow rate of 1.5 mL/min. The temperature for the detector and injector was fixed at 250° C. The oven temperature used for the analysis was 80° C. for 4 minutes, then it was increased at 20° C./min to 240° C. and held for 2 minutes.

Jet A-1, obtained by Air BP (Batch number BIS/HAL/12/035K), was dried by storing it over 3 Å molecular sieve for at least 24 hours. Standards with different water concentrations were prepared by adding measured volumes of distilled water by SGE µL syringes to 20 ml of anhydrous Jet A-1, taking extra care to inject the water in the middle of the solvent. Each standard was prepared just before use and ultrasonicated for 5 minutes to ensure an equal distribution of water.

A reactant solution was prepared to enable a simple, one-step addition of all the necessary chemicals. This solution was prepared by mixing 10 mL of triethyl orthoformate (reagent), 1 mL of 3-methylpentane (internal standard) and 7.1 µL of methanesulfonic acid (catalyst) in a GC vial obtained from Supelco (Bellefonte, USA) Because of contamination from the atmospheric moisture, it was necessary to prepare a new reactant solution each day.

For the analysis, 100 µL of reactant solution was added to 1 mL of a Jet A-1 sample in a 2 mL GC sample vial. To avoid water losses on the tip of the Gilson pipette used to measure the sample, the above mixture was used to rinse the tip of the pipette. All chemicals used in this experiment were purchased from Sigma Aldrich and, except the acid, distilled over anhydrous $MgSO_4$ and kept over 3 Å molecular sieve. All sample vials were cleaned with acetone and dried at 200° C. for 2 hours.

Experimental NMR [25]

Five buffers with constant acetic acid (AcOH) concentration and different $H^+$ concentrations were made by varying the amount of sodium acetate (AcONa) added (see Table 1). As the ionic concentration of the solution has an impact on the rate constant of hydrolysis, sodium chloride was added to keep the ionic strength constant in all 5 buffers [26].

TABLE 1

Buffer solutions in $H_2O$

| Buffer | [AcOH] | [AcONa] | [NaCl] |
|--------|--------|---------|--------|
| A | 0.192M | 0.3947M | 0.3693M |
| B | 0.192M | 0.192M | 0.572M |
| C | 0.192M | 0.0658M | 0.6982M |
| D | 0.192M | 0.048M | 0.716M |
| E | 0.192M | 0.0185M | 0.7455M |

The reaction samples were prepared directly in 5 mm NMR tube by adding 15 µL of TMOA in 500 µL of acetone-d6. To start the reaction 100 µL of acetic acid/sodium acetate aqueous buffer was added. All chemicals were purchased at the highest level of purity from Sigma Aldrich. Acetone-D6 and TMOA were dried before each experiment by distilling from 3 Å molecular sieve under nitrogen. Sodium chloride and sodium acetate were dried by heating them at T=100° C. for 4 hours under vacuum.

A 300 MHz NMR spectrometer was used to follow the concentration of TMOA with time by acquiring nine sequential $^1H$ NMR spectra every 10 min (actual delay time=10.38 min). Presaturation solvent suppression technique was used to obscure the $H_2O$ signal. An external reference was used by adding to the NMR tube a sealed capillary tube with 3-(trimethylsilyl)-1-propanesulfonic acid sodium salt dissolved in $D_2O$ (concentration=0.1966 M).

Figure 3:
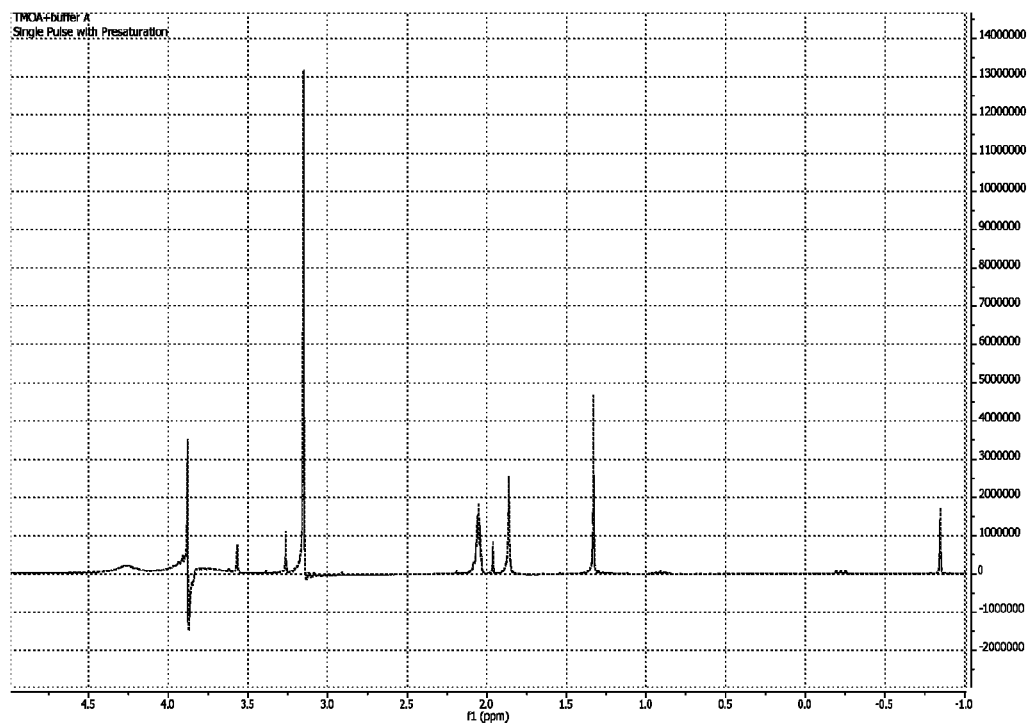
FIG. 3 Typical NMR spectra of TMOA in ACOM/AcONa buffer with TMS Salt.
Figure 7:
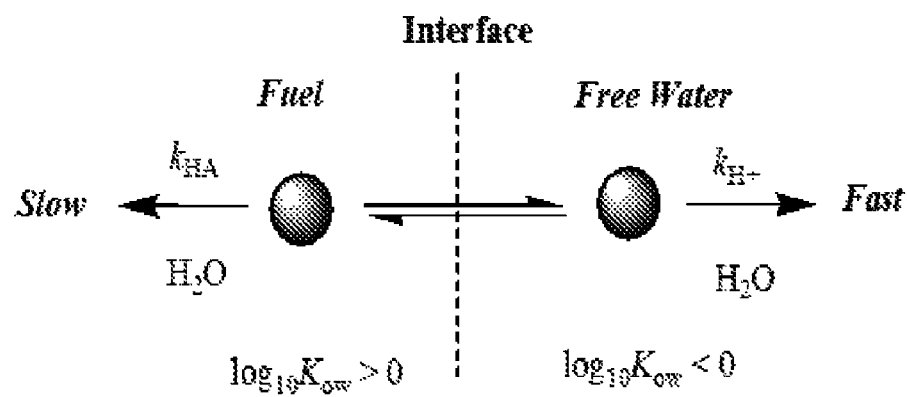
FIG. 7 Fuel water partitioning and the implications for acid catalysed hydrolysis. The water scavenger is represented by a sphere.
Figure 8:
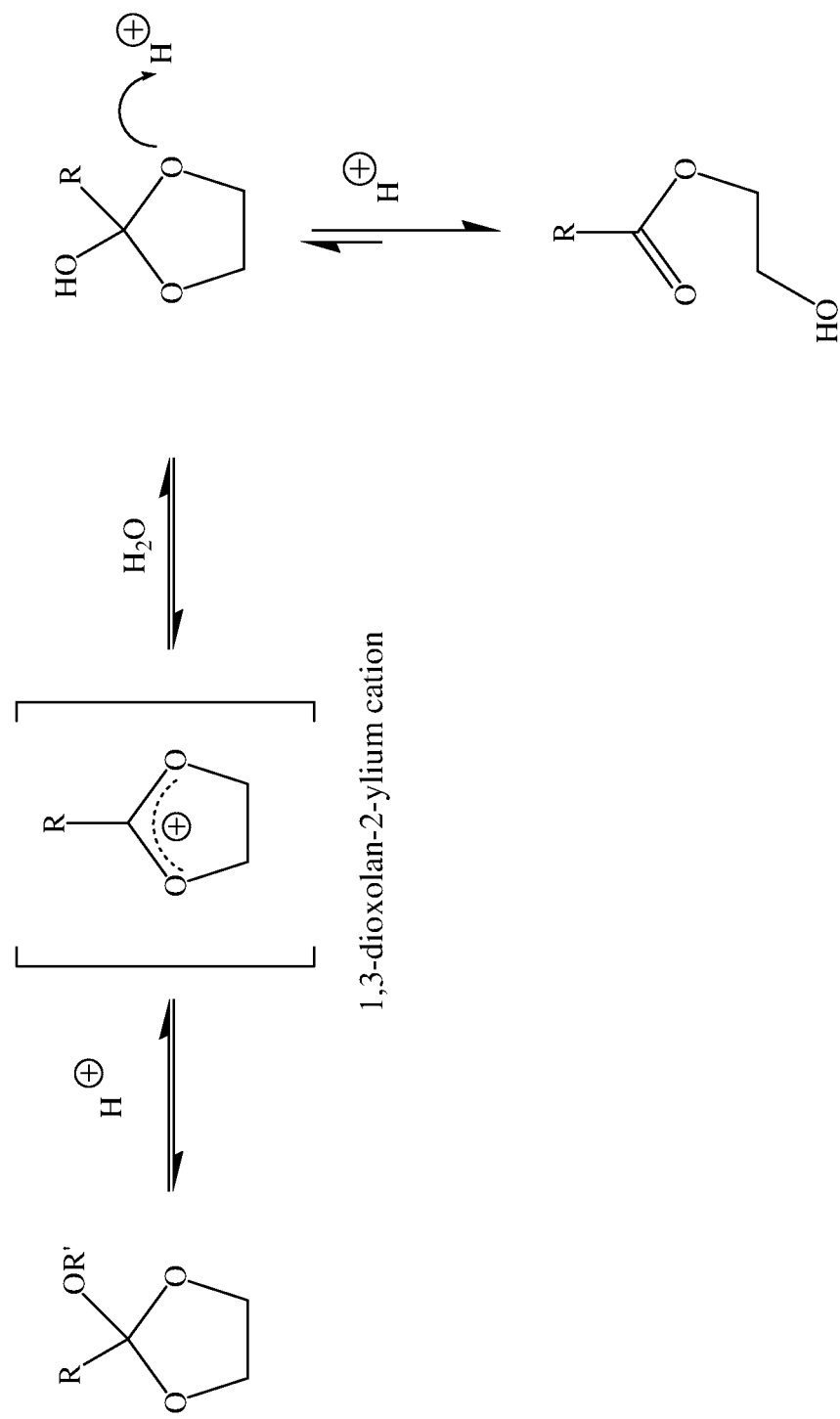
FIG. 8 The formation of 1,3,-dioxolan-2-ylium cations in water.

The TMOA $^1H$ NMR spectrum consists of two singlets resonating at 3.15 and 1.33 ppm, assigned to the —$OCH_3$ and —$CH_3$ residues, respectively (integrating 3:1—FIG. 7). The relative peak area (RPA—proportional to concentration) was measured by comparing the —$CH_3$ resonance with that of the external reference. See FIG. 3.

Figure 4:
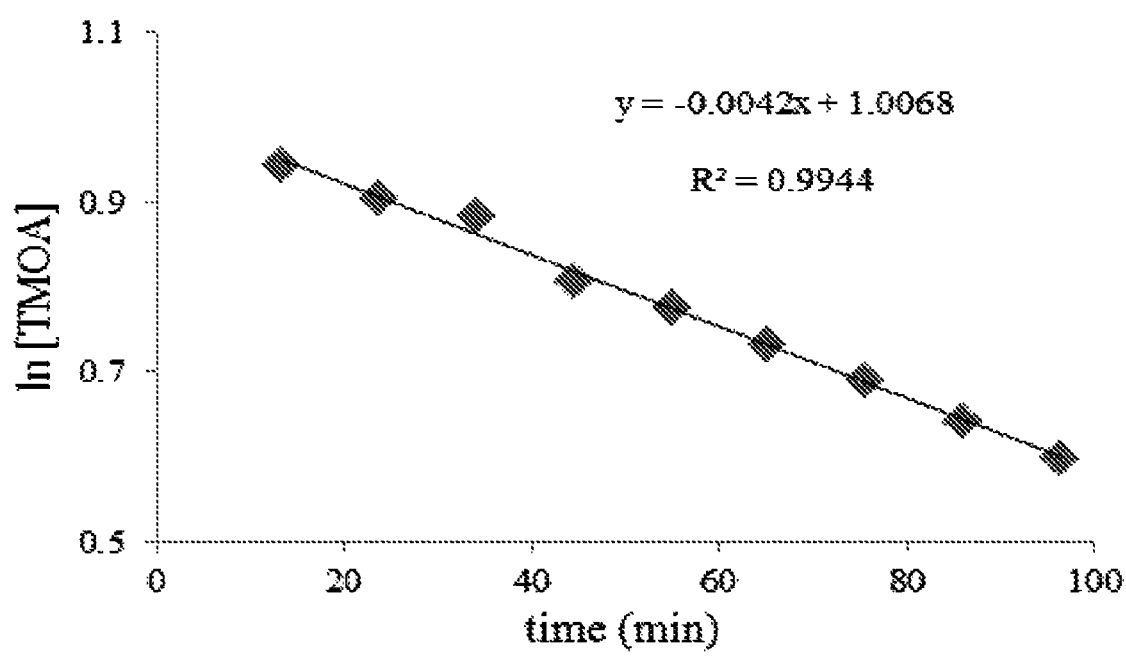
FIG. 4 Graph of kinetic data for reaction of TMOA with buffer D.

As an example, buffer D (pH=4.15) results are tabulated in Table 2 and they are represented in FIG. 4.

TABLE 2

Kinetic data for reaction of TMOA with buffer D.

| Time (min) | R.P.A. | In R.P.A. |
|------------|--------|-----------|
| 13.33 | 2.57 | 0.943906 |
| 23.71 | 2.47 | 0.904218 |
| 34.09 | 2.42 | 0.883768 |
| 44.47 | 2.24 | 0.806476 |
| 54.85 | 2.17 | 0.774727 |
| 65.23 | 2.08 | 0.732368 |
| 75.61 | 1.99 | 0.688135 |
| 85.99 | 1.9 | 0.641854 |
| 96.37 | 1.82 | 0.598837 |

Experimental Computational Study

In order to calculate log $K_{ow}$, two programs were used: KOWWIN™ and LogP (AB/LogP v2.0) from EPI suite and ACD/I-Lab, respectively [21, 22]. Both predict the log octanol-water partition coefficient by using an atom/fragment contribution method. The values reported in Table 2 are the averages of the two results.

For estimation of mammalian and environmental toxicology, a series of programs with well-established computational methods were used. Water solubility and dermal permeability (kp) of a compound were determined through its $K_{ow}$ by WSKOWWIN™ and DERMWIN, respectively. MPBPWIN™ estimated the vapor pressure of these chemicals through their boiling points [21].

The median lethal concentration ($LC_{50}$) for *Pimephales Promelas* was calculated with ACD/I-Lab program [22].

KOCWIN™ was used to predict carbon-normalized sorption coefficient for soil and sediment ($K_{OC}$) by using two different models: the Sabljic molecular connectivity method with improved correction factors and the traditional method based on log $K_{OW}$. Reported are the average values [21].

BIOWIN™ estimates aerobic and anaerobic biodegradability of organic chemicals using 7 different models. We have only considered the ultimate biodegradation timeframe, achieved when a material is totally utilized by microorganisms, and the ready biodegradability prediction [21].

Results & Discussion

Removing Free Water from Jet Fuel: Proof of Concept

Figure 2:
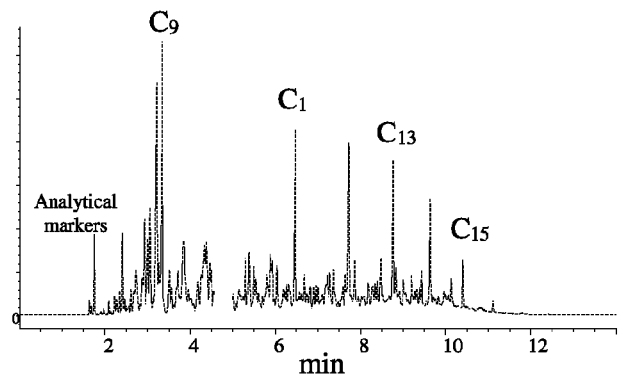
FIG. 2 shows a typical chromatogram of GC analysis of jet fuel showing the complex mixture of components of Jet A-1.

Because of the complexity of Jet A-1, there is a relatively narrow window of "visibility" in a GC chromatogram to observe analytical markers before the components of Jet A-1 begin to elute (<2 min at the conditions reported in the experimental section) (FIG. 2). A careful choice of methodology was therefore necessary before work could be undertaken in order to demonstrate the feasibility of using ortho esters as a dehydrating agents for jet fuel.

Chen et al. developed a useful analytical approach for measuring the water content of a range of hydrophobic solvents such as decane; a reasonable surrogate for jet A-1 [16]. The method relies upon the indirect determination of water via the GC measurement of ethanol (EtOH), a volatile side-product liberated via the acid-catalysed stoichiometric reaction of water with ortho ester 5 (Scheme 1).

Scheme 1. Hydrolysis of TEOF 5 catalysed by methane sulfonic acid (MsOH).

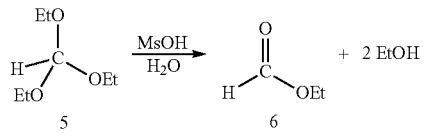

The GC method was adapted for measuring water in jet fuel (see experimental). Importantly—and as confirmed by GC-MS—the products of the hydrolysis of 5 i.e., ethanol, ethyl formate 6, in addition to the internal standard (3-methylpentane) elute before the components of jet fuel (FIG. 2). The retention times for ethanol and 3-methylpentane (internal standard) were 1.69 and 1.8 min, respectively.

Figure 5:
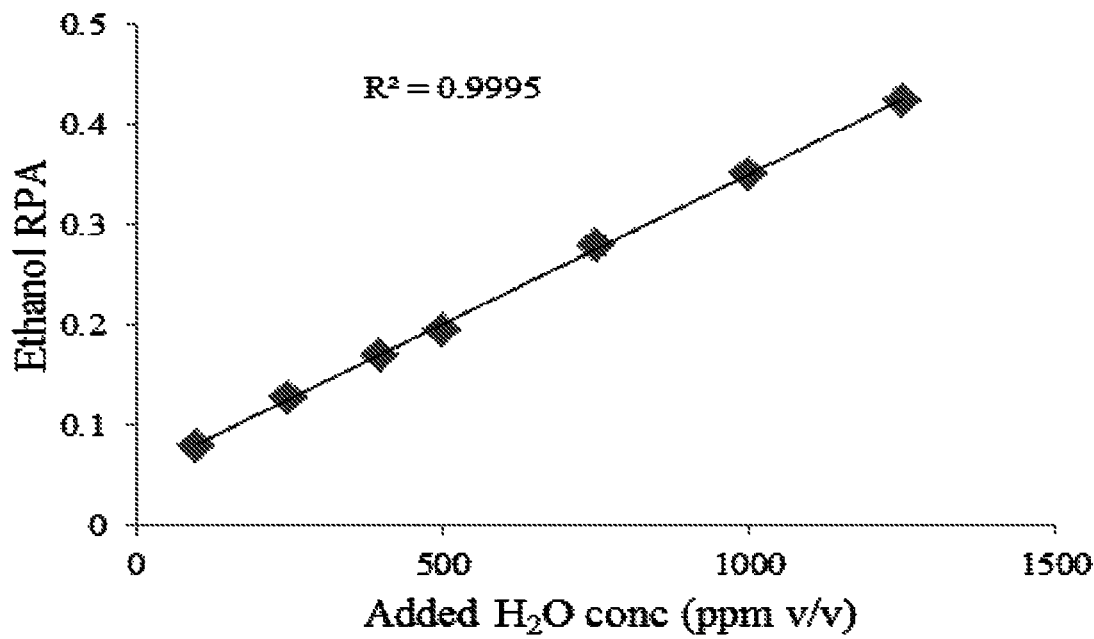
FIG. 5 Calibration curve of water correlation and relative peak are (RPA) for ethanol by GC.
Figure 6:
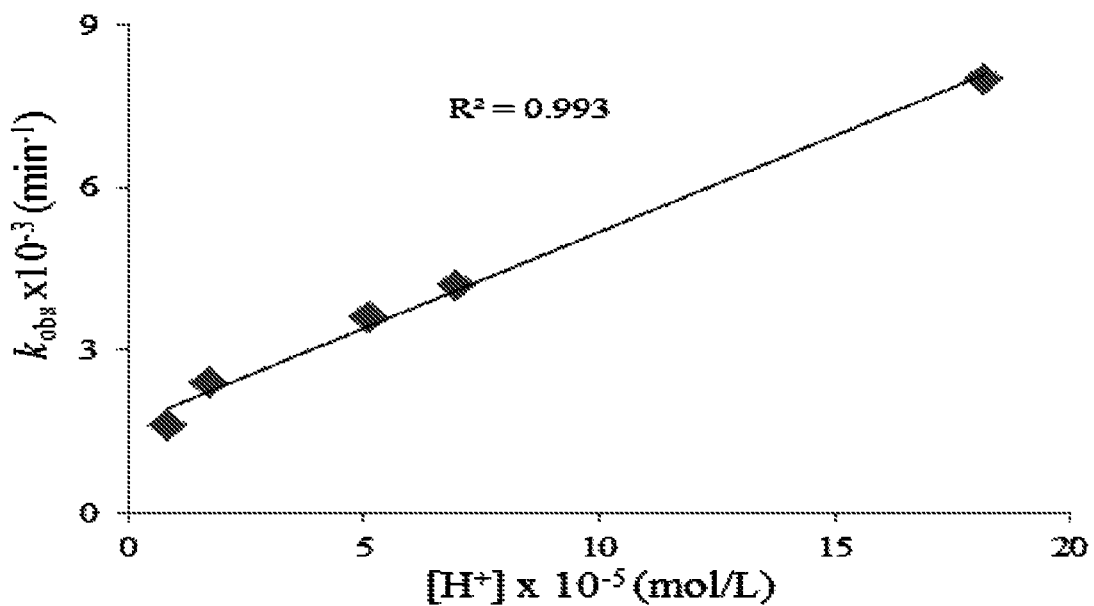
FIG. 6 Kobs v [H+] for TMOA.

For each water standard, the relative peak area (RPA) of ethanol was calculated by dividing the ethanol peak area by the internal standard peak area. To correct for atmospheric and residual water present in the reactant solution, the RPA of the reactant solution was subtracted from each ethanol RPA. A calibration curve was plotted, and is presented in FIG. 5.

As can be seen, an excellent linear correlation ($R^2$=0.9995%) exists between the ethanol RPA and water concentration in Jet A-1 in the concentration range examined (100-1250 ppm v/v).

In conclusion, the linearity of this relationship clearly illustrates the effectiveness of using triethyl orthoformate 5 as a dehydrating agent for Jet A-1. Importantly, the GC method reported here can be used to determine water concentrations in jet fuel beyond the accuracy of the industry standard—namely the Karl Fischer method [16].

As discussed in the introduction, jet fuel is mildly acidic, and indeed the batch of Jet A-1 used for these analyses is reported to be 0.01 mg KOH/g by ASTM D3242 [17]. In order to examine the capacity of 5 to dehydrate jet fuel in the absence of added acid, the GC method described here was repeated without methane sulfonic acid. In the absence of an added acid catalyst—with only the inherent acidity of jet fuel to catalyse the process—the reaction was found to be 60-75% complete after 2 days, compared to 100% completion in 30 minutes using methane sulfonic acid. Since a strong acid catalyst is undesirable inside the fuel tank of an aircraft, a kinetically faster process must be sought either through modifying the; (a) reaction conditions i.e., the nature of the acid catalyst, or (b) molecular structure of the ortho ester.

The Nature of the Acid Catalyst, and its Relationship to the Rate of Hydrolysis

Although there is still much to be uncovered about the acid catalysed hydrolysis of ortho esters, it is generally accepted that the process can be divided into two stages; namely, the formation of the water scavenging dialkoxy carbenium ion 11 from ortho ester 7, and the subsequent hydration and collapse of 11 to afford ester 13 (Scheme 2). The initial protonation of 7, and the subsequent formation of 11 is considered to be slow—and therefore rate determining—whereas the hydration of 11 and all subsequent steps en route to 13, are considered to be relatively fast [18, 19].

The protonation of 7, and the subsequent formation of 11 is subject to two clearly defined mechanisms; namely general (via undissociated acid HA)—and specific (via dissociated acid $H^+$) acid catalysis (Scheme 2) [18]. In the case of the former, H-A delivers a proton to an oxygen atom of the ortho ester, which then eliminates a molecule of alcohol ROH—via 10—to give 11 with and overall velocity constant $k_{HA}$. The cation is rapidly hydrated and ultimately collapses to ester 13 through several steps, and the ultimate elimination of a second molecule of ROH. In the case of specific acid catalysis, dissociated $H^+$ protonates the ortho ester 7 to afford—via 10—dialkoxy carbenium ion 11 with overall velocity constant $k_{H+}$. The fate of hydrated 11 is the same for both mechanistic pathways. It is clear therefore that the overall rate for the process observed in Scheme 2 will be dependent upon the slower of the two mechanistic pathways.

Scheme 2. General and specific acid catalyzed pathways for the hydrolysis of ortho esters.

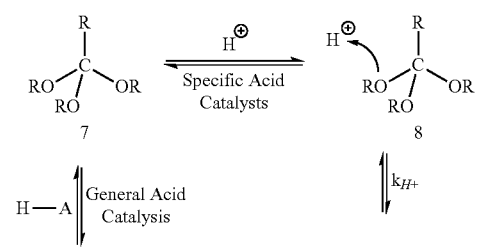

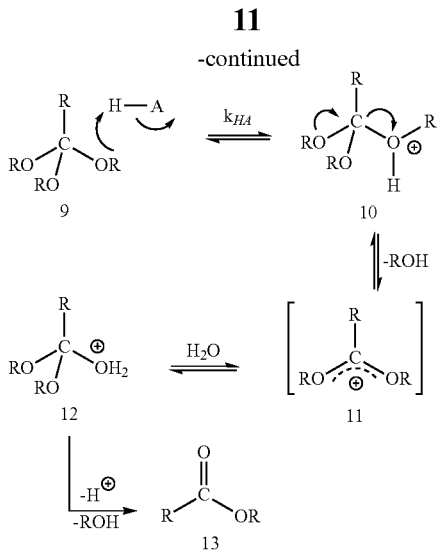

General acid catalysis is ordinarily facilitated by weaker, undissociated acids; conversely specific acid catalysis tends to be facilitated by stronger, fully dissociated acids. However, for all but the strongest acids both pathways will be operative. Given the physical environment in which we expect a water scavenger to operate—namely within the fuel tank of an aircraft—we sought to optimise the reaction velocity using the weakest acid possible. It was necessary therefore to determine the magnitude of the velocity constants associated with the simultaneous processes $k_{H+}$ and $k_{HA}$.

As mentioned earlier, jet fuel is mildly acidic. In the presence of polar solvents, such as water, the extent of the acid dissociation will be proportional to the acid dissociation constant ($K_a$) of the individual acids present (Eq. II).

$$K_a = \frac{[H^+][A^-]}{[HA]} \quad \text{(II)}$$

The approach adopted for determining $k_{H+}$ and $k_{HA}$, was to exploit the constancy of $K_a$ (=1.75×10⁻⁵ mol/L) whilst varying the numerators (i.e., [A⁻] 2→0.1 and pH 5.07→3.74) and maintaining [HA] constant (i.e., 0.192 mol/L). As the overall rate of reaction (equation III) is a summation of both processes described by $k_{H+}$ and $k_{HA}$, the rate constant $k_{obs}$ is therefore proportional to the concentration of both associated and dissociated acids (equation IV).

$$\text{rate} = k_{obs}[R-C(OR)_3] \quad \text{(III)}$$

$$k_{obs} = k_{H+}[H^+] + k_{HA}[HA] \quad \text{(IV)}$$

Given that [HA] is constant, expression IV becomes equivalent to that of a straight line and $k_{H+}$ and $k_{HA}$ may be determined by plotting $k_{obs}$ vs [H⁺]. To obtain $k_{obs}$ however, the rate equation integrated over time (Eq. V) must be used [14].

$$\ln[R-C(OR)_3]_t - \ln[R-C(OR)_3]_0 = -k_{obs}t \quad \text{(V)}$$

¹H NMR spectroscopy is the technique of choice when studying processes which occur on this timescale. Our choice of HA was acetic acid (AcOH), and five buffered solutions with different H⁺ concentration were prepared by varying the amount of sodium acetate (AcONa=A⁻). For the study, we switched focus from the aldehyde derivative TEOF (5, Scheme 1) used for the proof of concept study to the faster reacting keto-derivative trimethyl orthoacetate (TMOA) 8, Scheme 2 where R=—CH₃) for reasons of atom economy (20% lighter). For each buffered solution (see experimental) a $k_{obs}$ was obtained and the results presented in Table 3 and FIG. 5.

TABLE 3

| | Experimentally determined $k_{obs}$ | |
|---|---|---|
| [AcOH]/[AcONa] | [H⁺] (mol/L) | $K_{obs}$ (min⁻¹) |
| 0.486 | 8.51 × 10⁻⁶ | 1.6 × 10⁻³ |
| 1 | 1.75 × 10⁻⁵ | 2.4 × 10⁻³ |
| 2.918 | 5.11 × 10⁻⁵ | 3.6 × 10⁻³ |
| 4 | 7.00 × 10⁻⁵ | 4.2 × 10⁻³ |
| 10.378 | 1.82 × 10⁻⁴ | 8 × 10⁻³ |

From these data, $k_{obs}$ v. [H⁺] may be plotted (FIG. 5) and a straight line fitted (y=35.464x+1.6×10⁻³; R²=0.993) from which values for the gradient of the slope and y-intercept afford $k_{H+}$=35.5 min⁻¹ and, $k_{HA}$=7.8×10⁻³ min⁻¹ respectively. It is clear that the pathway catalysed by dissociated acid H⁺ (specific acid catalysis—scheme 2) is approximately 4500 times faster than the pathway catalysed by undissociated AcOH, within the pH range studied here (3.7→5.0).

The significant difference in the experimentally determined rate constants for the hydrolysis of an ortho ester by both dissociated H⁺ and associated HA acids has important implications for the partitioning behaviour of a scavenger across the fuel-free water interface (FIG. 7). Associated—relatively weak—acids (HA) tend to reside in the apolar environment of jet fuel, unlike the hydrophilic hydroxonium cation which by definition prefers the polar environment of free water. Our stated objective is to design a water scavenger (S) which preferentially partitions into the lipophilic fuel phase (i.e., $K_{ow}=[S]_{octanol}/[S]_{water}>0$, FIG. 7)—which in the case of an ortho ester means that here, it may only undergo a slow hydrolysis reaction with dissolved water—thereby ensuring fuel protection. However, at the phase boundary with free water, the water scavenger may encounter dissolved dissociated acid H⁺ and subsequently undergo a rapid hydrolysis reaction—thereby consuming free water.

Dual Purpose Water Scavengers

Cyclic ortho esters such as 14a-e (Scheme 3) present themselves as exciting, dual purpose agents because upon hydrolysis with water, the five membered ring (remembering atom economy) cleaves to afford hydrophilic alcohols of type 15a-e which incorporate as many sites for hydrogen bonding as the de-icer di-EGME (Scheme 3). Through manipulation of the substituent —R (14, Scheme 3, and Table 1) it is possible to fine-tune the lipophilicity of the water scavenger to ensure that it partitions preferentially into the fuel phase (i.e., consistent with $K_{ow}>0$). In order for the corresponding alcohol 15 produced by the hydrolysis of 14 to express de-icing properties it must be sufficiently hydrophobic to partition preferentially into residual free water ($K_{ow}<0$) [20]. There will clearly be a tipping point for the ideal dual-reagent as the lipophilicity of 14 and hydrophobicity of 15 as substituent —R varies through the series a→e.

Scheme 3. Hydrolysis of cyclic ortho esters 14a-e affords acyclic alcohols 15a-e.

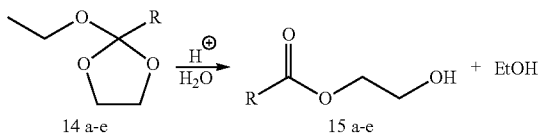

The commonly accepted measure of lipophilicity, log $K_{ow}$ [20] was calculated for compounds 14a-e and 15a-e, and the average values derived from two computational models are presented in Table 4 [21, 22]. Ethanol has experimentally and calculated log $K_{ow}$ values of −0.31 and −0.09, respectively [21-23].

TABLE 4

Calculated log $K_{ow}$ for cyclic ortho esters 14a-e and acyclic alcohols 15a-e.

| | R | 14 | 15 |
|---|---|---|---|
| a | —CH₃ | +0.97 | −0.55 |
| b | —CH₂CH₃ | +1.41 | −0.05 |
| c | —CH₂CH₂CH₃ | +1.78 | +0.42 |
| d | —CH₂CH₂CH₂CH₃ | +2.33 | +0.84 |
| e | —CH₂CH₂CH₂CH₂CH₃ | +2.88 | +1.54 |

As expected, when —R becomes progressively lipophilic down the series a→e, log $K_{ow}$ becomes increasingly positive which is consistent with favourable partitioning in fuel. Therefore it is anticipated that the series 14a-e possesses partitioning behaviour consistent with an effective water scavenger. However, in the case of the alcohols 15a-e, preferential partitioning in water is clearly indicated for 15a-b and 15c must be considered to be at the tipping-point for Jet fuel. Other structures may be used for other liquid hydrocarbons having different components.

In conclusion, calculations suggest that ortho esters 14a-c present themselves as water scavengers whose corresponding hydrolysis products 15a-e possess potential dual-action de-icing activity. In the next section, an evaluation of the mammalian and environmental toxicology of 14/15a-c is made.

Human and Environmental Toxicology

Well established computational methods (i.e., US EPA and ACD/I-La) have been used here to estimate and compare the human and environmental toxicity of 14/15a-c, and di-EGME [21, 22]. The results of these calculations are presented in Table 5; we compare estimated values for di-EGME because experimentally determined values for 13/14a-c are unavailable.

TABLE 5

Calculated human and environmental toxicological evaluations of di-EGME and 14/15a-c.

| | | 15 | | | 14 | | |
|---|---|---|---|---|---|---|---|
| Compounds | Di-EGME | a | b | c | a | b | c |
| Water solubility (mg/L, 25° C.) | $1 \times 10^6$ | $1 \times 10^6$ | $4.1 \times 10^5$ | $1.4 \times 10^5$ | $4.6 \times 10^3$ | $1.5 \times 10^3$ | $5.1 \times 10^2$ |
| Vapour Pressure (mmHg, 25° C.) | $1.1 \times 10^{-1}$ | $1.5 \times 10^{-1}$ | $1.7 \times 10^{-1}$ | $5.2 \times 10^{-2}$ | 4.8 | 1.8 | $6.9 \times 10^{-1}$ |
| Dermal Permeability Kp (cm/hr) | $5.4 \times 10^{-5}$ | $1.6 \times 10^{-4}$ | $2.9 \times 10^{-4}$ | $5.1 \times 10^{-4}$ | $2.9 \times 10^{-3}$ | $5.1 \times 10^{-3}$ | $9 \times 10^{-3}$ |
| $LC_{50}$ (mg/L) for *Pimephales Promelas* | $9.9 \times 10^3$ | $3.1 \times 10^3$ | $1.5 \times 10^3$ | $9.2 \times 10^2$ | $4.2 \times 10^3$ | $3.4 \times 10^3$ | $2.7 \times 10^3$ |
| Soil Adsorption Coefficient $K_{oc}$ (L/kg) | $7.4 \times 10^{-1}$ | 1.15 | 1.72 | 3.13 | 16.2 | 33.7 | 58.6 |
| Ultimate biodegradation timeframe | weeks | days-weeks | weeks | weeks | weeks-month | weeks-month | weeks-month |
| Ready biodegradability prediction | yes | yes | yes | yes | no | no | no |

Water solubility, vapour pressure, and dermal permeability were evaluated as potential measures of worker and consumer exposure. The median lethal concentration ($LC_{50}$) for *Pimephales promelas* was used to evaluate aquatic toxicity. Biodegradation, soil adsorption—along with water solubility—were used to estimate the environmental fate of compounds, and ultimately exposure to the general population.

In the first instance we will compare the calculated toxicity of de-icers 15a-c with di-EGME (Table 5). Both di-EGME and 15a-c are quite soluble in water—the former more so. As $K_p$ tends to increase with increasing lipophilicity, the inverse trend observed for water solubility would appear to be reflected in the greater dermal permeability of 15a-c. The vapour pressure of di-EGME and 15a-b are very similar—thereby posing similar risks to workers. The aquatic toxicities ($LC_{50}$) of 15a-b are of the same order of magnitude as di-EGME indeed all of the compounds in Table 3 fall well below the criteria for aquatic toxicity (i.e., >100 mg/L) [24]. Di-EGME and 15a-c are all weakly sorbing compounds $K_{oc}$<25 L/kg); importantly 15a-c are more likely than Di-EGME to adhere soil, and thereby not contribute to runoff.

The corresponding water scavengers 14a-c are relatively lipophilic compared to di-EGME, and as one would expect, possess greater dermal permeabilities, and their vapour pressures are also greater, posing marginally greater risk to workers. However, because 14a-c are dual-action agents, it is likely that the effective concentration required for jet fuel will be less than di-EGME—as will the ultimate level of exposure to workers. Ortho esters 14b-c in particular possess strong sorbing properties, and are less likely to contribute to runoff. Although ready biodegradability for 13a-c is not predicted, this does not take into account the likelihood that acidic soils will catalyze hydrolysis to 15a-c.

CONCLUSIONS

We have established that ortho esters are effective dehydrating agents for jet fuel. We have developed an analytical method—based upon the rapid hydrolysis of ortho esters—for determining the concentration of water in jet fuel. Detailed kinetic measurements using $^1$H NMR spectroscopy have established that ortho esters are rapidly hydrolysed by dissociated acid catalysts, whilst a slower process occurs with an associated acid catalyst. The implications for the development of a water scavenger are that lipophilic ortho esters will hydrolyse slowly in jet fuel, yet rapidly at the interface with free water. Cyclic ortho esters offer the potential for dual-purpose reagents which, upon hydrolysis, afford de-icers. Candidate substrates have been identified based upon their calculated partitioning behaviour and their human and environmental profiles have been assessed with respect to di-EGME.

REFERENCES

1. Coordinate Research Council, Technical Report no. 635, *Handbook of Aviation Fuel Properties, 3$^{rd}$ edition*, 2004.
2. Baena, S., Lawson, C. and Lam, J. K.-W., "Dimensional Analysis to Parameterise Ice Accretion on Mesh Strainers." *SAE Technical Paper* 2011-01-2795, 2011, doi: 10.4271/2011-01-2795.
3. Chevron Corporation, Technical Review, *Aviation Fuels Technical Review*, 2006.
4. Baena-Zambrana, S., Repetto, S. L., Lawson, C. P. and Lam, J. K.-W., "Behaviour of water in jet fuel-A literature review." *Progress in Aerospace Sciences*, 2013, doi: 10.1016/j.paerosci.2012.12.001.
5. Ministry of Defence, Defence Standard 91-91, *Turbine Fuel Aviation Kerosine Type, Jet A-1*. Issue 6, 2008.
6. Carpenter, M. D., Hetherington, J. L., Lao, L., Ramshaw, C. et al., "Behaviour of Water in Aviation Fuels at Low Temperatures." Presented at IASH 2011, USA, Oct. 16-20, 2011.
7. Lao, L., Ramshaw, C., Yeung, H., Carpenter, M. et al., "Behavior of Water in Jet Fuel Using a Simulated Fuel Tank." *SAE Technical Paper* 2011-01-2794, 2011, doi: 10.4271/2011-01-2794.
8. Taylor, S. E., "Component Interactions in Jet Fuels: Fuel System Icing Inhibitor Additive." *Energy & Fuels* 22(4): 2396-2404, 2008.
9. Trohalaki, S., Pachter, R. and Cummings, J. R., "Modeling of Fuel-System Icing Inhibitors." *Energy & Fuels* 13(5):992-998, 1999.
10. Mushrush, G. W., Beal, E. J., Hardy, D. R., Hughes, J. M. and Cummings, J. C., "Jet Fuel System Icing Inhibitors: Synthesis and Characterization." *Industrial & Engineering Chemistry Research* 38(6):2497-2502, 1999.
11. Sittig, M., "Handbook of Toxic and Hazardous Chemicals and Carcinogens." Noyes Publications, New Jersey, 1985.
12. Meshako, C. E., Bleckmann, C. A., and Goltz, M. N., "Biodegradability and Microbial Toxicity of Aircraft Fuel System Icing Inhibitors." *Environmental Toxicology* 14(4):383-390, 1999.
13. Mushrush, G. W., Stalick, W. M., Beal, E. J., Bash, S. C. et al., "The Synthesis of Acetals and Ketals of the Reduced Sugar Mannose as Fuel System Icing Inhibitors." *Petroleum Science and Technology* 15(3&4):237-244, 1997.
14. Atkins, P. W., "Physical Chemistry." 2$^{nd}$ edition, Oxford University Press, Oxford, UK, 1982.
15. Deslongchamps, P., Dory, I. L., and Li, S., "The Relative Rate of Hydrolysis of a Series of Acyclic and Six-Membered Cyclic Acetals, Ketals, Ortho esters and Orthocarbonates." *Tetrahedron* 56(22)3533-3537, 2000.
16. Chen, J. and Fritz, J. S., "Gas-Chromatographic Determination of Water after Reaction with Triethyl Orthoformate." *Analytical Chemistry* 6(18):2016-2020, 1991.
17. SGS Oil, "Jet A1 Full Test Report. Test Certificate No:AV12-00033.001." SGS UK Ltd, Bristol, UK, 2012.
18. Cordes, E. H. and Bull, H. G., "Mechanism and Catalysis for Hydrolysis of Acetals, Ketals, and Ortho Esters." *Chemical Reviews* 74(5):581-603, 1974.
19. Wenthe, A. M. and Cordes, E. H., "Concerning the Mechanism of Acid-Catalyzed Hydrolysis of Ketals, Ortho Esters, and Orthocarbonates." *Journal of the American Chemical Society* 87(14):3173-3180, 1965.
20. Chang, J. H., Beal E. J., Stalick, W. M. and Mushrush, G. W., "Fuel System Icing Inhibitors: the Synthesis of Esters of Oxaacids." *Petroleum Science and Technology* 16(9&10):979-1000, 1998.
21. US EPA, Estimation Programs Interface Suite™ for Microsoft® Windows (version 4.11), United States Environmental Protection Agency, Washington, USA, 2013.
22. ACD/I-Lab2 Predictor (version 5.0.0.184), Advanced Chemistry Development, Inc., Toronto, Canada, 2013.
23. Hansch, C., Leo, A. and Hoekman, D., "Exploring QSAR: Hydrophobic, Electronic, and Steric Constants." American Chemical Society, Washington, USA, 1995.
24. US EPA, "Estimating Aquatic Toxicity with ECOSAR." http://www.epa.gov/opot/sf/pubs/ecosar.pdf, 2013.
25. Ports, R. A. and Schaller, R. A., "Kinetics of the Hydrolysis of Orthoesters: A General Acid-Catalyzed Reaction." *Journal of Chemical Education* 70(5):421-424, 1993.
26. Bunton C. A. and Reinheimer, J. D., "Electrolyte Effects on the Hydrolysis of Acetals and Ortho Esters." *Journal of Physical Chemistry* 74(26):4457-4464, 1970.

The invention claimed is:

1. A liquid hydrocarbon comprising a dehydrating icing inhibitor selected from Formula I and Formula II, salts thereof or mixtures thereof;

Formula I

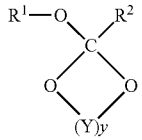

Formula II

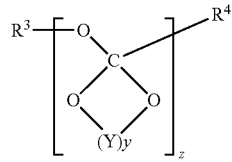

where:
R$^1$ and R$^3$ are independently selectable and are selected from a C$_1$ to C$_6$ substituted or non-substituted, branched or straight chain, alkyl or ether;

$R^2$ and $R^4$ are independently selectable and are selected from a $C_1$ to $C_7$ substituted or non-substituted, straight or branched chain, alkyl;

Y is independently selectable and is a substituted or non-substituted alkyl;

y is an integer of 1 to 3;

z is an integer of 2 to 6; and, wherein liquid hydrocarbon is a hydrocarbon fuel selected from an aviation fuel, gasoline, diesel and heating oil, a lubricant or a hydraulic fluid.

2. A liquid hydrocarbon according to claim 1, wherein the liquid hydrocarbon is a hydrocarbon fuel, lubricant, hydraulic fluid or hydrocarbon solvent.

3. A liquid hydrocarbon according to claim 2, wherein the hydrocarbon fuel is an aviation fuel, gasoline, diesel or heating oil.

4. A liquid hydrocarbon according to claim 1, wherein $R^1$ and $R^3$ are independently selected from $CH_3$—, $CH_3CH_2$—, $CH_3O(CH_2)_a$—, where a is an integer of 1 to 5, and an alkylene glycol or polyalkylene glycol containing 1 to 6 carbon atoms.

5. A liquid hydrocarbon according to claim 4, wherein $R^1$ or $R^3$ are $CH_3CH_2$—.

6. A liquid hydrocarbon according to claim 1, wherein $R^2$ and $R^4$ are independently selected from —$CH_3$, —$CH_2CH_3$, —$CH_2CH_2CH_3$, —$CH_2CH(CH_3)_2$ and —$CH_2C(CH_3)_3$.

7. A liquid hydrocarbon according to claim 1, wherein $R^3$ and $R^4$ are independently selected and are methyl or ethyl.

8. A liquid hydrocarbon according to claim 1, wherein y is 2.

9. A liquid hydrocarbon according to claim 1, wherein Y is independently selected from —$CH_2$— and —$CH(CH_3)$—.

10. A liquid hydrocarbon comprising a dehydrating icing inhibitor selected from Formula I and Formula II, salts thereof or mixtures thereof;

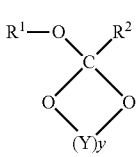

Formula I

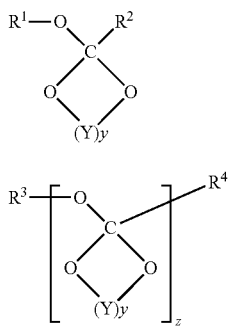

Formula II where:

$R^1$ and $R^3$ are independently selectable and are selected from a $C_1$ to $C_6$ substituted or non-substituted, branched or straight chain, alkyl or ether;

$R^2$ and $R^4$ are independently selectable and are selected from a $C_1$ to $C_7$ substituted or non-substituted, straight or branched chain, alkyl;

Y is independently selectable and is a substituted or non-substituted alkyl;

y is an integer of 1 to 3;

z is an integer of 2 to 6; where the dehydrating icing inhibitor has a Formula III or Formula IV or a salt thereof;

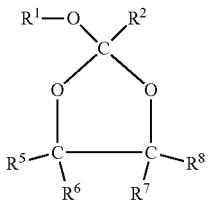

Formula III

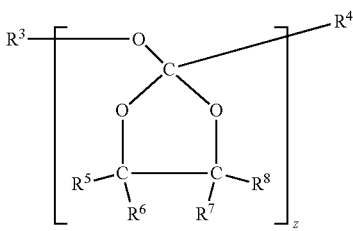

Formula IV wherein $R^5$ and $R^7$ are hydrogen; and $R^6$ and $R^8$ are methyl, and wherein $R^6$ and $R^8$ may be cis or trans relative to each other.

11. A liquid hydrocarbon according to claim 1, comprising 0.01 to 2% by volume of the dehydrating icing inhibitor.

12. A liquid hydrocarbon according to claim 1, wherein the compound is formed from a 1,3-dioxolan-2-ylium salt.

13. A method of inhibiting ice crystal formation in a liquid hydrocarbon comprising mixing the liquid hydrocarbon with a compound selected from Formula I and formula II, or mixtures thereof:

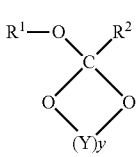

Formula I

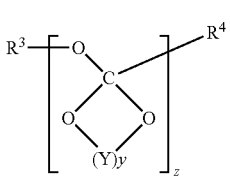

Formula II where:

$R^1$ and $R^3$ are independently selectable and are selected from a $C_1$ to $C_6$ substituted or non-substituted, branched or straight chain, alkyl or ether;

$R^2$ and $R^4$ are independently selectable and are selected from a $C_i$ to $C_7$ substituted or non-substituted, straight or branched chain, alkyl;

Y is independently selectable and is a substituted or non-substituted alkyl;

y is an integer of 1 to 3;

z is an integer of 2 to 6.

14. A method according to claim 13, wherein 0.01 to 2% by volume of the dehydrating icing inhibitor(s) is added to the liquid hydrocarbon.

15. A method according to claim 13, wherein the liquid hydrocarbon is a hydrocarbon fuel, lubricant, or hydrocarbon solvent.

16. A method according to claim 15, wherein the hydrocarbon fuel is an aviation fuel, gasoline, diesel of heating oil.

17. A method according to claim 13, wherein $R^1$ and $R^3$ are independently selected from $CH_3—$, $CH_3CH_2—$, $—CH_3O(CH_2)_a—$, where a is an integer of 1 to 5, and an alkylene glycol or polyalkylene glycol containing 1 to 6 carbon atoms.

18. A method according to claim 17, wherein $R^1$ or $R^3$ are $CH_3CH_2—$.

19. A method according to claim 13, wherein $R^2$ and $R^4$ are independently selected from $—CH_3$, $—CH_2CH_3$, $—CH_2CH_2CH_3$, $—CH_2CH(CH_3)_2$ and $—CH_2C(CH_3)_3$.

20. A method according to claim 13, wherein $R^3$ and $R^4$ are independently selected and are methyl or ethyl.

21. A method according to claim 13, wherein y is 2.

22. A method according to claim 13, wherein Y is independently selected from $—CH_2—$ and $—CH(CH_3)—$.

23. A method of inhibiting ice crystal formation in a liquid hydrocarbon comprising mixing the liquid hydrocarbon with a compound selected from Formula I and formula II, or mixtures thereof:

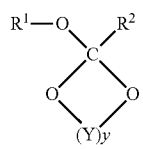

Formula I

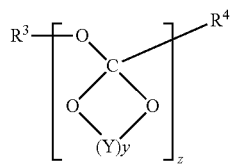

Formula II where:
R$^1$ and R$^3$ are independently selectable and are selected from a $C_1$ to $C_6$ substituted or non-substituted, branched or straight chain, alkyl or ether;

R$^2$ and R$^4$ are independently selectable and are selected from a $C_1$ to $C_7$ substituted or non-substituted, straight or branched chain, alkyl;

Y is independently selectable and is a substituted or non-substituted alkyl;

y is an integer of 1 to 3;

z is an integer of 2 to 6; wherein in dehydrating icing inhibitor has a Formula III or Formula IV or a salt thereof;

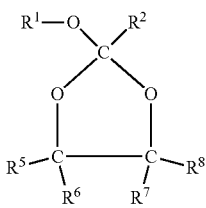

Formula III

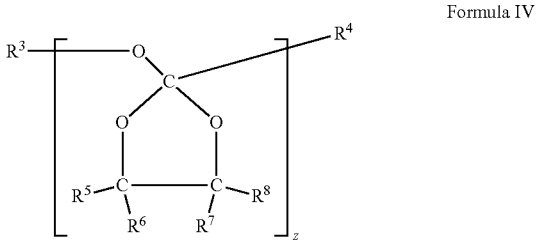

Formula IV wherein R$^5$ and R$^7$ are hydrogen; and R$^6$ and R$^8$ are methyl, and wherein R$^6$ and R$^8$ may be cis or trans relative to each other.

24. A method of inhibiting ice crystal formation in a liquid hydrocarbon comprising mixing the liquid hydrocarbon with a 1,3-dioxolan-2-ylium salt.

25. A compound of Formula IV or a salt thereof;

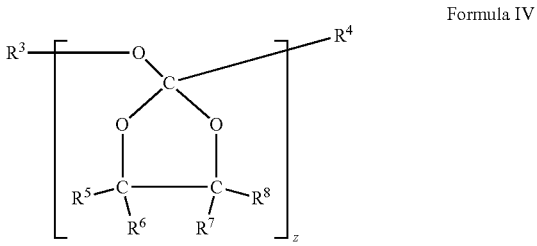

Formula IV where:
R$^3$ is independently selectable and is selected from a $C_1$ to $C_6$ substituted or non-substituted, branched or straight chain, alkyl or ether;

R$^4$ is independently selectable and is selected from a $C_1$ to $C_7$ substituted or non-substituted, straight or branched chain, alkyl;

z is an integer of 2 to 6;

R$^5$ and R$^7$ are hydrogen;

and R$^6$ and R$^8$ are methyl, and wherein R$^6$ and R$^8$ may be cis or trans relative to each other as a dehydrating icing inhibitor.

* * * * *